United States Patent
Herrmann

(10) Patent No.: US 9,678,220 B2
(45) Date of Patent: Jun. 13, 2017

(54) X-RAY DETECTOR WITH SATURATED SENSOR ELEMENT ESTIMATED PHOTON COUNTING

(71) Applicant: KONINKLIJKE PHILIPS N.V., Eindhoven (NL)

(72) Inventor: Christoph Herrmann, Aachen (DE)

(73) Assignee: KONNINKLIJKE PHILIPS N.V., Eindhoven (NL)

( * ) Notice: Subject to any disclaimer, the term of this patent is extended or adjusted under 35 U.S.C. 154(b) by 355 days.

(21) Appl. No.: 14/362,429

(22) PCT Filed: Dec. 6, 2012

(86) PCT No.: PCT/IB2012/057009
§ 371 (c)(1),
(2) Date: Jun. 3, 2014

(87) PCT Pub. No.: WO2013/093684
PCT Pub. Date: Jun. 27, 2013

(65) Prior Publication Data
US 2014/0328465 A1    Nov. 6, 2014

Related U.S. Application Data

(60) Provisional application No. 61/577,322, filed on Dec. 19, 2011.

(51) Int. Cl.
*G01N 23/04* (2006.01)
*G01T 1/17* (2006.01)
(Continued)

(52) U.S. Cl.
CPC .............. *G01T 1/17* (2013.01); *G01N 23/04* (2013.01); *G01T 1/208* (2013.01); *G01T 1/247* (2013.01); *G01T 1/2985* (2013.01)

(58) Field of Classification Search
CPC .......... A61B 6/00; A61B 6/4014; A61B 6/42; A61B 6/4208; A61B 6/4241;
(Continued)

(56) References Cited

U.S. PATENT DOCUMENTS

| 4,037,104 A * | 7/1977 | Allport | ................ G01B 15/025 |
| | | | 250/308 |
| 6,759,658 B2 * | 7/2004 | Overdick | ............. G01N 23/046 |
| | | | 250/336.1 |

(Continued)

FOREIGN PATENT DOCUMENTS

| WO | 2007010448 A2 | 1/2007 |
| WO | 2009072056 A2 | 6/2009 |
| WO | 2010043926 A2 | 4/2010 |

OTHER PUBLICATIONS

Roessl, E., et al.; A comparative study of a dual-energy-like imaging technique based on counting-integrating readout; 2011; Med. Phys.; 38(12)6416-6428.

*Primary Examiner* — Anastasia Midkiff

(57) ABSTRACT

The present invention relates to an x-ray detector comprising a sensor unit for detecting incident x-ray radiation comprising a number of sensor elements, a counting channel per sensor element for obtaining a count signal by counting photons or charge pulses generated in response to the incident x-ray radiation since a beginning of a measurement interval, an integrating channel per sensor element for obtaining an integration signal representing the total energy of radiation detected since the beginning of the measurement interval, and a processing unit for estimating, from the integration signals of the sensor elements, count signals of sensor elements whose counting channel has been saturated during the measurement interval.

15 Claims, 6 Drawing Sheets

(51) Int. Cl.
*G01T 1/20* (2006.01)
*G01T 1/24* (2006.01)
*G01T 1/29* (2006.01)
*G01T 1/208* (2006.01)

(58) Field of Classification Search
CPC ......... A61B 6/4266; A61B 6/48; A61B 6/482;
A61B 6/52; A61B 6/5205; A61B 6/58;
A61B 6/582; A61B 6/585; A61B 6/586;
A61B 2560/00; A61B 2560/02; A61B
2560/0223; A61B 2560/0266; A61B
2560/0276; A61B 2562/00; A61B
2562/02; A61B 2562/06; A61B 2576/00;
G01T 1/00; G01T 1/15; G01T 1/16;
G01T 1/1603; G01T 1/20; G01T 1/2018;
G01T 1/24; G01T 1/247; G01T 1/36;
G01T 1/361; G01T 1/362; G01T 1/366;
G06T 7/00; G06T 7/0002; G06T 7/0012;
G06T 2207/00; G06T 2207/10; G06T
2207/10072; G06T 2207/10081; G06T
2207/10084; G06T 2207/10016; G06T
2207/20; G06T 2207/20148; G06T
2207/20172; G06T 2207/30168; G06T
2210/00; G06T 2210/52; H01L 27/00;
H01L 27/14; H01L 27/142; H01L 27/144;
H01L 27/1446; H01L 27/146; H01L
27/14601; H01L 27/14603; H01L
27/14605; H01L 27/14609; H01L
27/14634; H01L 27/14641; H01L
27/14643; H01L 27/14658; H01L
27/14661; H01L 27/14676; H01L 27/148;
H01L 27/14806; H01L 27/14812; H01L
27/14831; H01L 27/1485; H01L
27/14856; H04N 5/30; H04N 5/32; H04N
5/335; H04N 5/3355; H04N 5/357; H04N
5/365; H04N 5/3651; H04N 5/3653;
H04N 5/367; H04N 5/369; H04N 5/372;
H04N 5/37206; H04N 5/3725; H04N
5/374; H04N 5/3742; H04N 5/3743;
H04N 5/3745; H04N 5/37455; H04N
5/378

See application file for complete search history.

(56) References Cited

U.S. PATENT DOCUMENTS

| | | | |
|---|---|---|---|
| 7,433,443 B1 | 10/2008 | Tkaczyk et al. | |
| 7,894,576 B2* | 2/2011 | Carmi | G01T 1/17 378/98.9 |
| 8,592,773 B2* | 11/2013 | Baeumer | G01T 1/17 250/370.09 |
| 2001/0048080 A1 | 12/2001 | Meulenbrugge | |
| 2006/0208195 A1 | 9/2006 | Petrick et al. | |
| 2008/0069297 A1* | 3/2008 | Hoffman | A61B 6/032 378/19 |
| 2008/0099689 A1* | 5/2008 | Nygard | G01T 1/2018 250/370.09 |
| 2009/0304149 A1* | 12/2009 | Herrmann | A61B 6/4233 378/62 |
| 2010/0012845 A1* | 1/2010 | Baeumer | G01T 1/362 250/361 R |
| 2012/0032085 A1* | 2/2012 | Baeumer | G01T 1/1647 250/362 |
| 2012/0085915 A1* | 4/2012 | Baeumer | G01T 1/17 250/370.09 |

* cited by examiner

X-RAY DETECTOR WITH SATURATED SENSOR ELEMENT ESTIMATED PHOTON COUNTING

CROSS REFERENCE TO RELATED APPLICATIONS

This application is a national filing of PCT application Serial No. PCT/IB2012/057009, filed Dec. 6, 2012, published as WO 2013/093684 A2 on Jun. 27, 2013, which claims the benefit of U.S. provisional application Ser. No. 61/577,322 filed Dec. 19, 2011, which is incorporated herein by reference.

FIELD OF THE INVENTION

The present invention relates to an x-ray detector and a corresponding x-ray detection method. The present invention relates further to an x-ray device comprising an x-ray detector, to a processor and processing method for use in an x-ray device having an x-ray detector and to a computer program for implementing said processing method.

BACKGROUND OF THE INVENTION

Photon-counting based spectral CT systems for examining an object, e.g. a patient or a material, such as a tyre or cast part, require detectors, which can deal with the high count rate generated in today's energy-integrating CT systems. The commonly used direct conversion material is not fast enough to deal with the high count rates, which can occur in such systems. In particular, detector pixels behind the object close to the direct beam ("surface beams") or directly seeing the direct beam usually see such a high count rate that they are saturated, i.e. they do not provide a usable counting signal, especially not with sufficient energy-information; for simplicity, the term "surface beams" here also comprises beams, which are so weakly attenuated that they cause pixels to see too high a count rate, although geometrically these beams are not close to the surface of the object. This can mean on the one hand that due to the very high count rate pulses can no longer be distinguished from each other, i.e. the pixels (also called "sensor elements" of the sensor included in the detector hereinafter) are saturated (such a pixel or sensor element is also called a "piled-up pixel" hereinafter). On the other hand, it can mean that due to massive charge trapping a part or all of the volume of the detector pixels become polarized, i.e. the internal electric field breaks down so that electron-hole pairs generated in the crystal due to interaction with x-ray photons are no longer efficiently separated.

In the latter situation it is difficult or even impossible to gain correct information from the measurement data, neither with a photon-counting detector nor with an energy-integrating detector, since due to the weakened electric field the majority of the electron-hole pairs generated in an x-ray interaction is not collected so that the energy information is unpredictably corrupted. However, in the first situation (i.e. case of a "saturated" or "piled-up" pixel or sensor element), a solution seems possible which is provided by the present invention.

SUMMARY OF THE INVENTION

It is an object of the present invention to provide an x-ray detector and a corresponding detection method which enable providing accurate and reliable measurement data even in case the counting channels of some of the sensor elements have been saturated and, thus, cannot directly provide a reliable count signal.

It is a further object of the present invention to provide an x-ray device, a processor and processing method for use in an x-ray device having an x-ray detector and to a computer program for implementing said processing method.

In a first aspect of the present invention an x-ray detector is presented that comprises
 a sensor unit for detecting incident x-ray radiation comprising a number of sensor elements,
 a counting channel per sensor element for obtaining a count signal by counting (x-ray) photons or charge pulses generated in response to the incident x-ray radiation since a beginning of a measurement interval,
 an integrating channel per sensor element for obtaining an integration signal representing the total energy of radiation detected since the beginning of the measurement interval, and
 a processing unit for estimating, from the integration signals of the sensor elements, count signals of sensor elements whose counting channel has been saturated during the measurement interval.

In a further aspect of the present invention an x-ray device is presented comprising an x-ray source for emitting x-ray radiation, an x-ray detector according to the present invention, and a reconstruction unit for reconstructing an image from the estimated count signals of saturated sensor elements and the obtained count signals of non-saturated sensor elements.

In a still further aspect of the present invention a processor is presented for use in an x-ray device having an x-ray detector comprising a sensor unit for detecting incident x-ray radiation comprising a number of sensor elements, a counting channel per sensor element for obtaining a count signal by counting (x-ray) photons or charge pulses generated in response to the incident x-ray radiation since a beginning of a measurement interval and an integrating channel per sensor element for obtaining an integration signal representing the total energy of radiation detected since the beginning of the measurement interval, said processor comprising:
 a processing unit for estimating, from the integration signals of the sensor elements, count signals of sensor elements whose counting channel has saturated during the measurement interval, and
 a reconstruction unit for reconstructing an image from the estimated count signals of saturated sensor elements and the obtained count signals of non-saturated sensor elements.

In yet another aspects of the present invention, there is provided an x-ray detection method, a processing method and a computer program which comprises program code means for causing a computer to perform the steps of the processing method when said computer program is carried out on a computer.

Preferred embodiments of the invention are defined in the dependent claims. It shall be understood that the claimed methods, processor, and computer program have similar and/or identical preferred embodiments as the claimed detector and as defined in the dependent claims.

The present invention thus proposes to use an x-ray detector having a sensor with sensor elements (pixels), which provide both the number of counts above one or more energy thresholds and at the same time an integrating measurement result (preferably in each pixel). The integrating measurement results provide information of the total charge received by the separate sensor elements of the detector during a measurement interval which may, for instance, be useful in case of a large quantum flows. However, the integrating measurement results are further used to rather accurately estimate the count signals with energy information of sensor elements whose counting channel has been saturated during the measurement interval (those sensor elements being commonly referred to as "saturated sensor elements" or "pile-up pixels").

With this modified set of counting channel measurement results (some of them obtained from the estimation for saturated sensor elements, the others obtained in real measurements), the usual data evaluation processes, e.g. a reconstruction of an image, can be applied, for instance an Extended Alvarez-Macovsky decomposition for K-edge imaging or a reconstruction bin-by-bin for each energy bin.

In an embodiment said processing unit is adapted for
determining an object model from the obtained integration signals of the sensor elements, and
determining the count signals of saturated sensor elements from said object model.

The object model can thus be obtained by reconstructing the signals of the integrating channel in each pixel, which object model provides some estimate of the object's material composition as well as the path lengths of the x-ray beams especially for surface beams. While the count signals of non-saturated sensor elements may be used in addition, they are generally not needed to determine the object model and/or to determine the count signals of saturated sensor elements.

Having the object model available, in a further embodiment said processing unit is adapted for determining the count signals of saturated sensor elements by
modeling x-ray beams incident on said saturated sensor elements from the object model and the spectrum of the x-ray beams in front of the object and
determining the count signals of the saturated sensor elements from the modeled x-ray beams of the respective saturated sensor elements.

Here, "in front of the object" means the side of the object facing the x-ray source, i.e. before the x-ray beams hit the object. According to this embodiment the (known or measured) spectrum of x-ray beams in front of the object is taken, which x-ray beams terminate in the saturated pixels. These (determined) x-ray beams are then attenuated by using an attenuation factor for the individual x-ray beams (or groups of x-ray beams) derived from the object model. This provides the beam spectrum incident to the saturated detector pixel. Thus, a quite accurate estimation of the count signals of the saturated sensor elements can be obtained.

In other words, according to this embodiment the object model is used to mimic (in terms of energy spectrum) those x-ray beams behind the object (i.e. on the side of the object facing the detector). Such x-ray beams go along very weakly absorbing paths through the object so that the incident count rate is so high that pile-up increases the level that can be corrected for, which beams cause the detecting pixel's counting channels to be saturated. The modelled x-ray beam for a certain pixel is then used to determine a modelled measurement result for the counting channel of the considered pixel.

Preferably, direct beam signals are derived in each pixel from air scans (i.e. measurement results) with limited flux, such that none of the pixels is saturated. These direct beam signals are then upscaled to the flux values used in the measurements with the object. With this approach, there is no need for a scout scan (i.e. a low dose scan of the object to get an estimate of the object properties, e.g. precise geometry, usually used for dose optimization) to determine the object model. The object model is obtained from the data acquisition of a single scan, which also provides the intended image or images (for instance in case of K-edge imaging).

Preferably, said counting channel comprises at least one discriminator, in particular at least two discriminators, for counting photons or charge pulses at different energy levels since a beginning of a measurement interval and obtaining energy dependent count signals since a beginning of a measurement interval. Generally, at least two discriminators are used, but it may also be possible to obtain spectral information from the counting channel with one threshold only in combination with the integrating channel. For instance, two different measurements allow for doing a photo-compton decomposition or a two-material decomposition, which is the simple case of Alvarez-Makovsky decomposition, as e.g. described in WO 2007/010448 A2. From the energy dependent count signals different kinds of image information may be reconstructed, e.g. image information about coronary vessels including the thickness of contrast medium contained in these vessels, so that the lumen size can be quantified as well as the thickness of calcified vessel areas allowing for assessing calcifications.

The sensor unit can be implemented using different technologies. In one embodiment said sensor unit comprises a direct-conversion sensing layer for directly converting incident x-ray radiation into electrical charge signals forming charge pulses. Preferably, said sensor unit further comprises an integrating layer representing said integrating channel, said integrating layer being arranged on a side of the direct-conversion sensing layer facing away from the incident x-ray radiation for converting x-ray radiation reaching said integrating layer into said integration signals.

Detectors having such a direction-conversion sensing layer and/or an integrating layer and the technology for making them is generally known in the art. For instance, WO 2009/072056 A2 discloses a monolithically integrated crystalline direct-conversion semiconductor detector for detecting x-radiation incident to a detector surface exposed to an irradiation with x-rays as well as a method for manufacturing such a direct-conversion semiconductor detector. In the introductory portion of this document various types and technologies of detectors are described, which can generally be used in the sensing unit of the present invention.

Further, WO 2007/010448 A2 describes an x-ray detector has a sensor absorbing x-ray quanta of polychromatic spectra and generating an electric sensor signal corresponding to the absorbed x-ray quanta. There is at least one counting channel including a plurality of discriminators each counting a number of charge signals detected at a different respective threshold since a beginning of a measurement interval and an integrating channel which measures overall charge of the charge signals detected since the beginning of the measurement interval.

The content of these documents, particularly the description of the detectors, is herein incorporated by reference.

Preferably, in an embodiment said processing unit is adapted for estimating an integration signal of a sensor element, at which insufficient x-ray radiation is reached on the integrating layer, by interpolating integration signals of neighboring sensor elements or by extrapolating the count signal of said sensor element. In this way sufficient measurement data for reconstructing an image with sufficient detail are obtained.

In another embodiment said sensor unit comprises an indirect sensing arrangement for first converting incident x-ray radiation into (optical) photons and then converting said (optical) photons into electrical charge signals. Such an indirect sensing arrangement is also generally known in the art. For instance, an FDXD detector including a scintillator layer for converting x-rays into light and photodiodes for converting the light into electric charges is described in US 2001/0048080 A1. The content of this document, particularly the description of the detector, is herein incorporated by reference as well.

Still further, in an embodiment said sensor unit comprises a direct-conversion sensing arrangement for directly converting incident x-ray radiation into electrical charge signals forming charge pulses and an indirect sensing arrangement for first converting incident x-ray radiation into photons and then converting said photons into said integration signals.

While generally the integration signals of the sensor elements are sufficient for determining, e.g. by use of the above described object model, the count signals of saturated sensor elements, in an embodiment the processing unit is adapted for estimating the count signals of the saturated sensor elements from the count signals of non-saturated sensor elements and the integration signals of the sensor elements. For instance, there is the concept of truncated reconstruction, when measurement signals of certain beams are missing, which concept does not use the integration signals but also the count signals of the non-saturated sensor elements are used for estimating the count signals of the saturated sensor elements.

The x-ray device may be a (medical or industrial) x-ray apparatus, e.g. having a fixed arrangement of the x-ray source and the x-ray detector or a C-arc on which the x-ray source and the x-ray detector are mounted, or a CT apparatus, e.g. a photon-counting energy-resolving (human) CT apparatus. In an embodiment of the x-ray device at least two x-ray sources and at least two x-ray detectors are provided, each being arranged for detecting radiation emitted by one of the at least two x-ray sources, wherein at least one detector is adapted for performing count measurements to provide count signals and at least one other detector is adapted for performing integrated measurements to provide integration signals.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
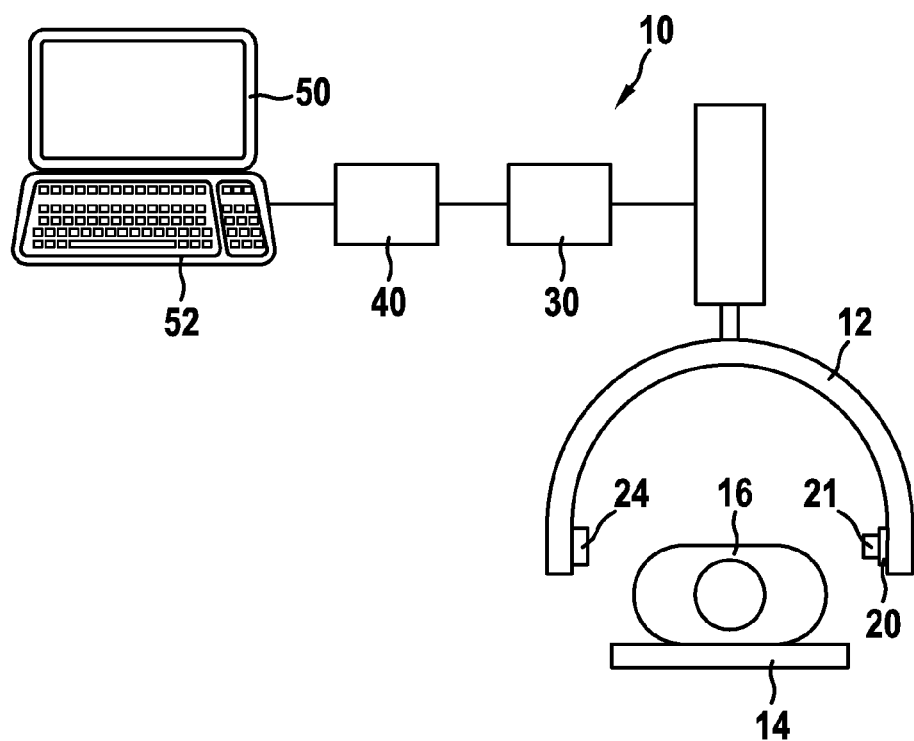
FIG. 1 shows a first embodiment of an x-ray device according to the present invention.

FIG. 1 shows a first embodiment of an x-ray device according to the present invention, in particular a CT (Computed Tomography) scanner 10 designed as a C-arm x-ray apparatus. The CT scanner 10 (which may also look differently, e.g. in the form of a tube having a ring-shaped support) includes a support 12 and a table 14 for supporting a patient 16. The support 12 includes an x-ray source assembly 20 that projects a beam of x-rays, such as a fan beam or a cone beam, towards a x-ray detector 24 on an opposite side of the support 12 while a portion of the patient 16 is positioned between the x-ray source assembly 20 and the x-ray detector 24.

The x-ray source assembly 20 may be configured to deliver radiation at a plurality of energy levels, and the x-ray detector 24 may be configured to generate image data in response to radiation at different energy levels. The x-ray source assembly 20 may include a collimator 21 for adjusting a shape of the x-ray beam. The collimator 21 may include one or more filters (not shown) for creating radiation with certain prescribed characteristics. The x-ray detector 24 has a plurality of sensor elements (221; see FIG. 2) configured for sensing a x-ray that passes through the patient 16. Each sensor element generates an electrical signal representative of an intensity of the x-ray beam as it passes through the patient 16. The support 12 may be configured to rotate about the patient 16. In another embodiment, the support 12 may be configured to rotate about the patient 16 while they are standing (or sitting) in an upright position. The positioning of the support 12 and patient 16 are not limited to the examples illustrated herein, and the support 12 may have other configurations (e.g., positions or orientations of an axis of rotation), depending on a position and orientation of a body part for which imaging is desired.

In the illustrated embodiment, the CT scanner 10 also includes a processor 40, a monitor 50 for displaying data, and an input device 52, such as a keyboard or a mouse, for inputting data. The processor 40 is coupled to a control 30. The rotation of the support 12 and the operation of the x-ray source assembly 20 are controlled by the control 30, which provides power and timing signals to the x-ray source assembly 20 and controls a rotational speed and position of the support 12 based on signals received from the processor 40. The control 30 also controls an operation of the x-ray detector 24. For example, the control 30 can control a timing of when image signal/data are read out from the x-ray detector 24, and/or a manner (e.g., by rows or columns) in which image signal/data are read out from the x-ray detector 24. Although the control 30 is shown as a separate component from the support 12 and the processor 40, in alternative embodiments the control 30 can be a part of the support 12 or the processor 40. The processor 40 may further comprise a reconstruction unit for reconstructing one or more images from the detected x-ray radiation.

During a scan to acquire x-ray projection data (i.e., CT image data), the x-ray source assembly 20 projects a beam of x-rays towards the x-ray detector 24 on an opposite side of the support 12, while the support 12 rotates about the patient 16. In one embodiment, the support 12 makes a 360 degree rotation around the patient 16 during image data acquisition. Alternatively, if a full cone detector is used, the CT scanner 10 may acquire data while the support 12 rotates 180 degrees plus the fan beam angle. Other angles of rotation may also be used, depending on the particular system being employed. In one embodiment, the x-ray detector 24 is configured to generate at least 900 frames of images in less than 1 second. In such a case, the support 12 only needs to rotate around the patient 18 once in order to collect sufficient amount of image data for reconstruction of computed tomography images. In other embodiments, the x-ray detector 24 may be configured to generate frames at other speeds.

The patient 16 is positioned such that the positioning is disposed between the x-ray source assembly 20 and the x-ray detector 24. After a prescribed time (e.g., 150 seconds) measured from the point of contrast injection has lapsed, the support 12 then rotates about the patient 16 to generate two sets of image data. The two sets of image data may be generated in quick succession (e.g., within 5 to 20 milliseconds) using radiation at different levels, or within any time period as long as the first and the second sets of image data are captured fast enough to render the object being imaged to appear motionless. As the support 12 rotates about the patient 16, the x-ray source assembly 20 emits radiation. In one embodiment the radiation is emitted at a single energy level or at a broad energy range. In another embodiment the radiation is emitted alternately at a first and a second (or even more) energy level, particularly having a first energy level that is below a k-absorption edge (K-edge) of the contrast agent and a second energy level that is above the k-edge of the contrast agent. The emitted radiation is attenuated by the patient 16 and impinges on the x-ray detector 24.

The x-ray detector 24 generates image signals/data in response to radiation impinging thereon. Additional sets of image data for different support angles can be generated as the support 12 rotates about the patient. After a desired amount of image data (e.g., sufficient for reconstruction of volumetric image) have been generated, the image data can be stored in a computer readable medium for later processing, e.g. on a hard disk.

Figure 2:
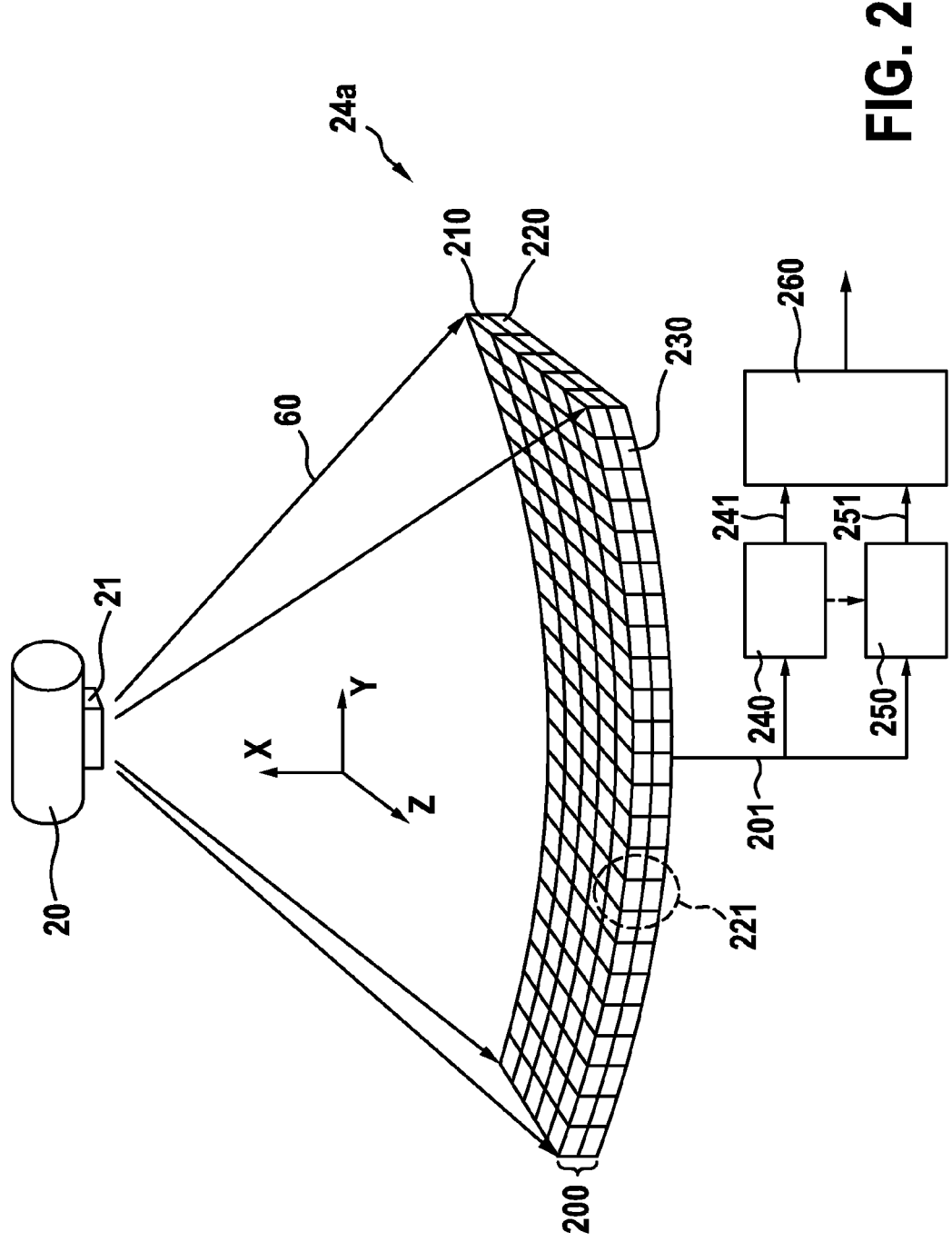
FIG. 2 shows a first embodiment of an x-ray detector according to the present invention.

The x-ray detector 24 can be constructed in various ways. FIG. 2 shows an exemplary x-ray detector 24a comprising an imager (also called sensor unit) 200 that includes a x-ray conversion layer 210 made from a scintillator element, such as Cesium Iodide (CsI), and a photo detector array 220 (e.g., a photodiode layer) coupled to the x-ray conversion layer 210. The x-ray conversion layer 210 generates light photons in response to x-ray radiation, and the photo detector array 220, which includes a plurality of detector elements 221, is configured to generate electrical signal in response to the light photons from the x-ray conversion layer 210. The x-ray conversion layer 210 and the photo detector array 220 may both be pixelated, thereby forming a plurality of imaging elements 230, or the x-ray conversion layer 210 may be non-pixelated. The imager 200 may have a curvilinear surface (e.g., a partial circular arc). Such surface configuration is beneficial in that each of the imaging elements 230 of the imager 200 is located substantially the same distance from the x-ray source 20 assembly. The imager 200 can alternatively have a rectilinear surface or a surface having other profiles. Each imaging element 230 (or pixel) may have a cross sectional dimension that is approximately 200 microns or more, and more preferably, approximately 400 microns or more, although imaging elements having other dimensions may also be used. Preferred pixel size can be determined by a prescribed spatial resolution. Imaging elements 230 having 200 to 400 microns in cross sectional dimension are good for general anatomy imaging, while other cross sectional dimensions may be preferred for specific body parts. The imager 200 can be made from amorphous silicon, crystal and silicon wafers, crystal and silicon substrate, or flexible substrate (e.g., plastic), and may be constructed using flat panel technologies (e.g., active-matrix flat panel technologies) or other techniques known in the art of making imaging device.

Each of the imaging elements 230 may comprise a photodiode (forming part of the detector element 221) that generates an electrical signal in response to a light input. The photodiode receives light input from the x-ray conversion layer 210 that generates light in response to x-rays 60. The photodiodes are connected to an array bias voltage to supply a reverse bias voltage for the imaging elements. A transistor (such as a thin-film N-type FET) functions as a switching element for the imaging element 230. When it is desired to capture image data from the imaging elements 230, control signals are sent to a gate driver to "select" the gate(s) of transistors. Electrical signals from the photodiodes "selected" by the gate driver are then sent to charge amplifiers, which outputs image signals/data for further image processing/display.

In one embodiment, the image data are sampled from the imaging elements 230 one line at a time. Alternatively, the image data from a plurality of lines of the imaging elements 230 can be sampled simultaneously. Such arrangement reduces the time it takes to readout signals from all lines of imaging elements 230 in the imager 200. This in turn, improves a frame rate (i.e., number of frames that can be generated by the imager 200 per second) of the imager 200.

During use, radiation impinges on the x-ray detector 24a, which then generates image signals/data in response to the radiation. For instance, radiation at a first energy level impinges on the x-ray detector 24a, which then generates image signals/data in response to the radiation at the first energy level. After the image signals/data are read out from the photo detector array 220, radiation at a second energy level is directed to the detector assembly 24a. The assembly 24a then generates image signals/data in response to the radiation at the second energy level.

In one embodiment, one or more filters can be placed between the x-ray source assembly 20 and the x-ray detector 24 (e.g., on top of the conversion layer 210) before radiation is directed to the x-ray detector 24a. The filter(s) alters radiation exiting from the patient 16, such that radiation having a desired characteristic will be received by the x-ray detector 24a. In one embodiment, a first filter(s) can be used to maximize or optimize a detective quantum efficiency of the x-ray detector 24a for radiation at a first energy level, while a second filter(s) can be used to maximize or optimize detective quantum efficiency of the x-ray detector 24a for radiation at a second energy level. For example, the x-ray detector 24a may have a uniform sensitivity to all photon energies in a spectrum, may have a sensitivity that is proportional to photon energy, or may have "holes" where photons of certain energy ranges are not efficiently absorbed. For each of these different types of x-ray detector 24a, one or more filters can be selected to maximize an efficiency of the system 10 (e.g., maximizing a response of the system 10 in measuring the injected contrast agent, and/or minimizing dose delivery and time). The placement of the filter(s) can be accomplished manually or mechanically. In some embodiments, the filters can be parts of the x-ray detector 24.

Such an x-ray detector 24a is generally known in the art and is, for instance, described in more detail in WO 2007/010448 A2 or US 2001/0048080 A1.

In alternative embodiments, the x-ray detector may use different detection schemes. For example, in alternative embodiments, instead of having the x-ray conversion layer, the x-ray detector can include an imager having a photoconductor (direct-conversion material), which generates electron-hole-pairs or charges in response to x-rays so that no photo-diode is needed.

The majority of the x-ray quanta is absorbed in the sensor assembly so as to be converted, after absorption, into an electric charge signal whose magnitude is approximately proportional to the absorbed energy. In the present context, it is not important whether the conversion of the x-ray quanta into the charge signals takes place directly (by means of so-termed directly converting materials, for example, gases such as Xe, semiconductors such as GaAs, CdTe, CdZnTe, or photoconductors such as Se, $PbI_2$ or PbO) or indirectly (for example, by conversion into low energy light quanta by means of a scintillating material and subsequent detection by a photodiode of crystalline or amorphous silicon).

The x-ray detector according to the present invention further comprises a counting channel 240 per sensor element for obtaining a count signal 241 with energy information by counting photons or charge pulses generated in response to the incident x-ray radiation since a beginning of a measurement interval and an integrating channel 250 per sensor element for obtaining an integration signal 251 representing the total energy of radiation detected since the beginning of the measurement interval. Further a processing unit 260 is provided for estimating count signals of sensor elements whose counting channel has been saturated during the measurement interval from the integration signals of the sensor elements. These data are then provided to the reconstruction unit (e.g. a separate unit, such as a processor, or the processor 40 including means for performing a reconstruction) for reconstructing an image from the estimated count signals of saturated sensor elements and the obtained count signals of non-saturated sensor elements. This will be explained below in more detail.

Figure 3:
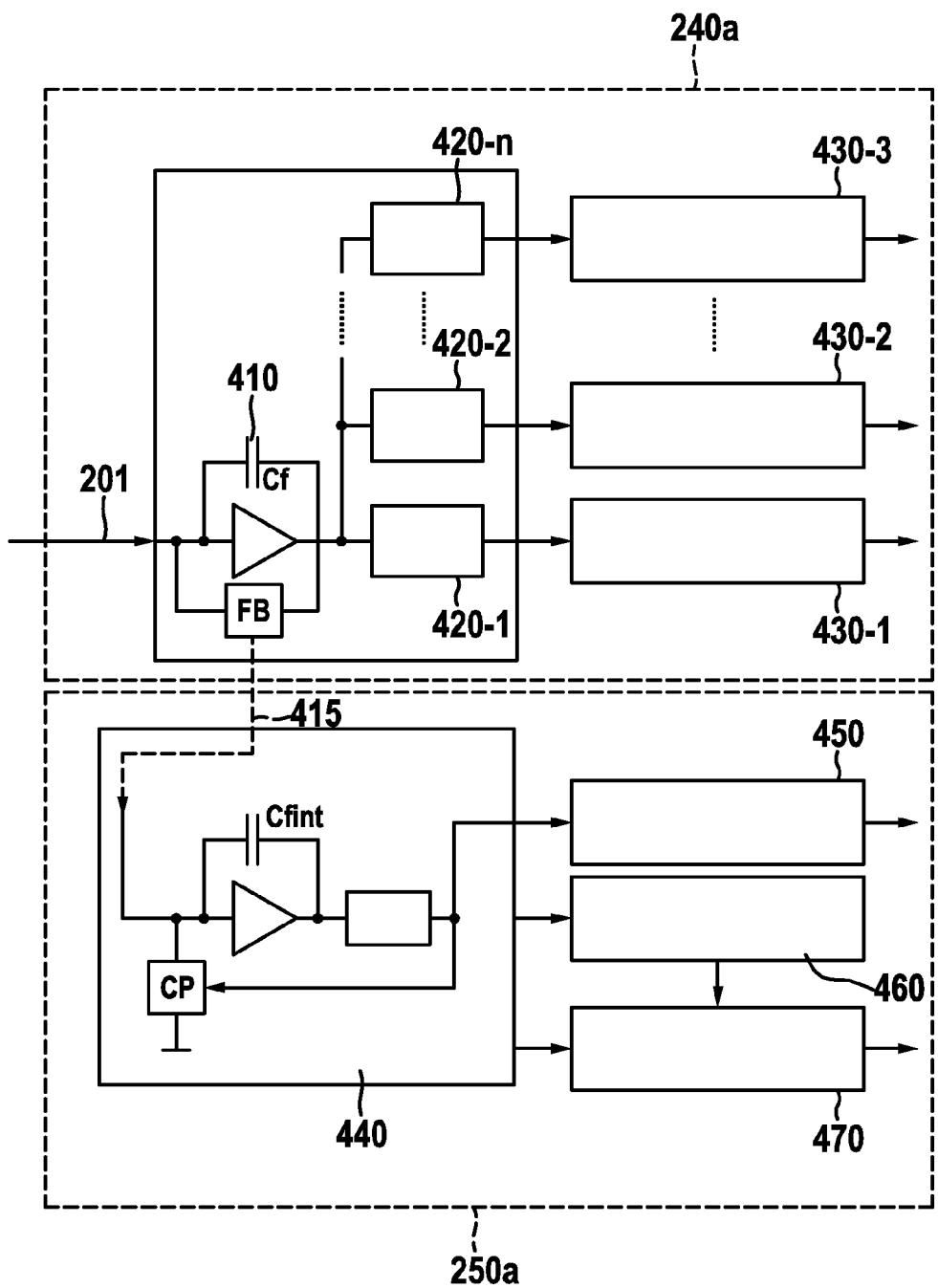
FIG. 3 shows more details of the x-ray detector shown in FIG. 2.

FIG. 3 shows an embodiment of circuit architecture of the components of a counting channel 240a and an integrating channel 250a of the proposed x-ray detector in each sensor pixel. The circuitry may be realized as an integrated circuit, for example, as a CMOS circuit. In this embodiment the electric signals 201 generated by the sensor unit 200 are applied to an input pre-amplifier 410 of the counting channel 240a. The input pre-amplifier 410 converts the sensor signals 201 into a different signal (for example, a voltage signal). It may be a charge sensitive amplifier (CSA), that is, typically an integrated circuit which includes a bleeding resistor. For each brief charge pulse at the input of pre-amplifier 410, an exponentially decreasing voltage is produced at the output, the surface area below this exponential curve being proportional to the charge within the pulse.

In order to have multiple threshold counting functionality, one or more (here a plurality of) discriminators 420-1 to 420-n are connected to the output of the preamplifier 410. Each of the discriminators may consist of a signal shaping amplifier and a comparator with an adjustable threshold value and generates a digital output signal (counting pulse) for each charge pulse from the sensor which is larger than a predetermined quantity of charge. The lowest threshold (which may be implemented by discriminator 420-1) distinguishes counts generated by photons with minimum energy from counts generated by noise (e.g. electronic noise). The higher thresholds can be used for K-edge imaging. For example, with two discriminators, discriminator 420-2 may represent a threshold which corresponds to pulse sizes generated by the pre-amplifier 410 in response to sensor signals, which were generated by photons above the energy (K-edge energy), at which the K-edge of the used contrast medium is found.

In order to determine the photons with energy below the K-edge energy, the difference between the values of event counter 430-2 and event counter 430-1 is computed, while the photons with energy above the K-edge energy are given by the value of event counter 430-2. The counters 430-1 to 430-n may be electronic digital counters with a counting depth of n bits. Linearly fed back shift registers may be used to save space.

In this embodiment an integrating channel unit 440 of the integrating channel 250a receives a signal 415 from a feedback loop of preamplifier 410 and may be an "overall signal acquisition circuit" which detects the total quantity of charge indicated by the sensor signal during an integration period. This circuit may be realized by an integrator circuit with an analog output, and a voltage/frequency converter, or it may be realized in some other manner.

Using the additional integrating channel unit 440 rather than only a number of different counting channel (which would result in an energy resolving pulse counter) may be seen in the fact that the integration is done over the whole energy range so that the evaluation will not be quantum-limited, while this could well occur for some of the bins of an energy resolving pulse counter, especially if the energy-bin size is small, i.e. only few photons are counted per energy bin on average.

Optional charge packet counter 450 and time counter 460 determine an optimized estimation for the electrical charge generated during a measurement interval marked by time latch 470, which charge is proportional to the energy deposited by x-rays during the measurement interval. The count of the counters 430-1 to 430-n, and the result of the integration in integrating channel 440 are provided to the data processing unit 260 (see FIG. 2). The data processing unit 260 can thus evaluate the results of the counting channel as well as the integrating channel.

In a first embodiment of the proposed detector according to the present invention the concept as explained above with respect to FIGS. 2 and 3 is used, in which, in each pixel, there is a counting channel with one or more (in particular n) thresholds and an integrating channel, which both evaluate the same signal coming from a direct-conversion sensor pixel.

Due to the assumption that none of the sensor pixels is polarized, however some pixels see too much pile-up ("piled-up pixels") so that counting with sufficient energy information is no longer possible, each pixel is still able to provide an integrating measurement result. With the integrating measurements, a "conventional" integrating slice image of the object can be reconstructed in the processing unit 260, which already gives a rough estimate of the material decomposition of the object (e.g. to indicate where are bones, where is soft-tissue, possibly also in which vessels is contrast agent). From these pieces of information a rough estimate of the attenuation coefficient in each pixel can be obtained, and even an estimate of the energy resolution (for instance, some a-priori knowledge of the material may be available, e.g. a vessel filled with a known contrast agent could be modeled by the contrast agent with some "educated guess" assumption of the contrast agent concentration) as well as the geometric information, especially the lengths of the paths, which each x-ray beam goes through the object for each view. With the obtained coarse object model, estimated counting measurement results can be derived for all "piled-up" detector pixels from a simulation using the known x-ray spectrum in front of the object, the path lengths through the object, and the coarse information on the object composition on these paths through the object.

These simulated counting measurement results of a few "piled-up" pixels together with the measured energy-resolved counting results of the many other pixels, which are not saturated, the usual data evaluation processes can be applied, for instance an extended Alvarez-Macovsky decomposition for K-edge imaging as described in WO 2007/010448 A2 or reconstruction bin-by bin in the reconstruction unit 40 (see FIG. 1).

Figure 4:
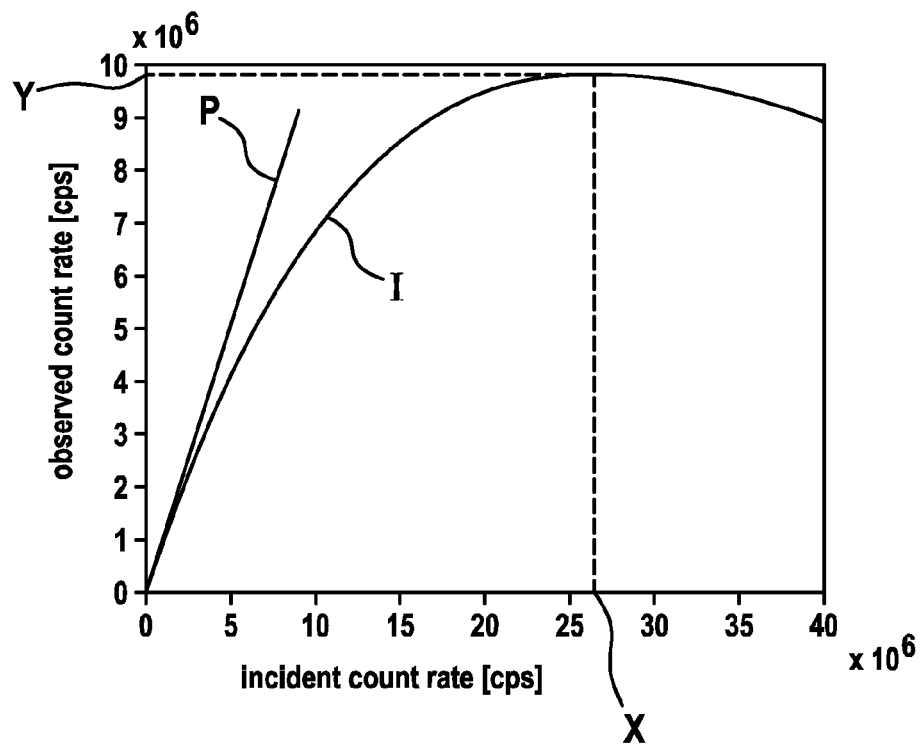
FIG. 4 shows a diagram depicting the observed count rate vs. incident count rate according to another embodiment.

In another embodiment, it may be possible to still reconstruct an approximately correct image using the counting signals of "piled-up pixel" (i.e. of the lowest threshold so that no energy information is available), while the integrating signal of a pixel provides an indication for pile-up in this pixel so that counting signals (without energy-information) of piled-up pixels are corrected for, e.g. based on a correction scheme using the paralyzable deadtime model of a detector according to "Glenn Knoll, Radiation detection and measurement, 3rd edn (New York: Wiley) p. 119-122". This is illustrated by the diagram shown in FIG. 4 depicting the observed count rate vs. incident count rate for Poissonian (curve P) and equidistant inter-arrival times (I) of adjacent pulses for the example of a dead time of 37.6 ns. Y indicates the maximum observable count rate, and X indicates the corresponding incident count rate, at which the maximum observable count rate is reached. The integrating measurement allows for deciding, whether the incident count rate is bigger or smaller than the one corresponding to the maximum observable count rate of the paralyzable count rate curve of x-ray photons, which stochastic count process follows a Poisson distribution, sometimes called "Poisson arrivals".

The counting image reconstructed just from counting signals without energy information in each pixel is then used to model the object in weakly absorbing regions to mimic the incident x-ray spectrum of the piled-up pixels.

If there are a very small number of polarized pixels, it may be possible to obtain the object model by just interpolating the missing integrating measurement results for these pixels from neighbor pixels.

For regions in the object, which are close to the object surface, there are generally many other beams, which pass through this region with quite strong attenuation, so that for reconstructing this region, the "model signals" only represent a small subset of all signals, which are available in reconstructing these regions.

In the pixels, where both the integrating and the counting channel works, even both measured signals can be used e.g. for doing the extended Alvarez-Macovsky decomposition as described in WO 2007/010448 A2.

The known problem of the direct conversion materials Cd[Zn]Te to exhibit a high after-glow in integrating mode can be addressed by using a grid switched tube, such that the afterglow can be measured and compensated for.

Generally, it is possible to implement the approach described above with reference to FIG. 3 also with a fast scintillator. In this case, exactly the same approach as above is possible and necessary, since there will still be "piled-up" pixels, i.e. pixels, in which only an integrating signal can be obtained with sufficiently small error.

Figure 5:
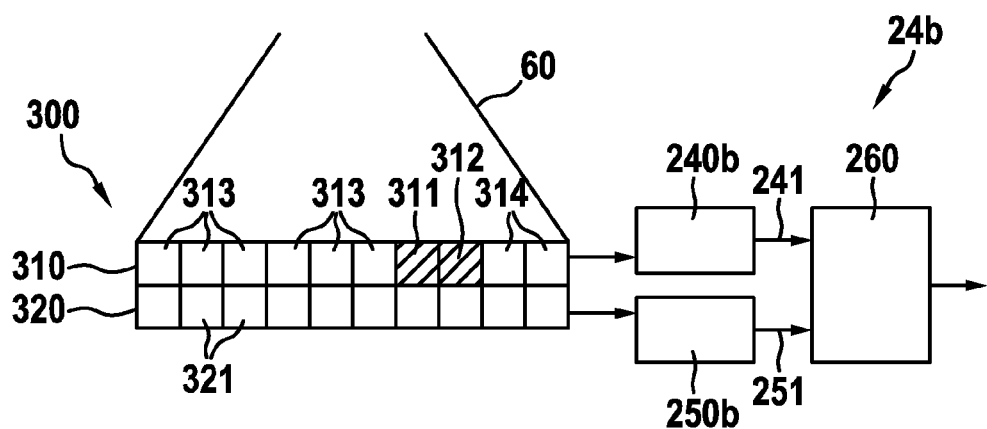
FIG. 5 shows a second embodiment of an x-ray detector according to the present invention.

Another embodiment of the proposed detector 24*b* is shown in FIG. 5. This detector 24*b* comprises a sensor unit 300 having at least a (direct conversion material based) counting layer 310 (e.g. with n thresholds) and a terminating integrating layer 320, which can be used in a similar manner as described above. Again, a counting channel 240*b* and an integrating channel 250*b* per sensor element is provided to provide counting signals 241 and integrating signals 251. As indicated in the counting layer 310 some sensor elements (pixels) 311, 312 are saturated ("piled-up"), i.e. while the other sensor elements 313, 314 are not saturated. To be more precise, the counting channels of the marked sensor elements 311, 312 are saturated in this example, while the counting channels of the other sensor elements of the counting layer 310 are not saturated.

Since the integrating layer 320 can be made of a scintillator, there will not be the problem of detector pixels, which do not provide any integration signal due to polarization, since the scintillator works at much higher x-ray fluxes than the direct conversion material, and the scintillator does not show polarization phenomena (there is no internal electrical field, which can be weakened by trapped electrons or holes). The pixels 311, 312 are hit by x-ray beams 60, which only see a weakly absorbing path through the object (usually surface beams), and thus exhibit pile-up (or even polarization) in the counting layer 310. Due to the high flux, there are still sufficient photons, which are absorbed in the terminating integrating layer 320 so that all sensor elements 321 can provide integration signals. Other pixels hit by x-ray beams 60, which see a stronger absorbing path through the object, can both count in the counting layer 310, and integrate in the terminating integrating layer 320. Hence, the object model can again be determined by the integrating measurements obtained in each pixel.

There may be pixels, in which the integration signal 251 is very weak, since the absorption on the path through the object is very high. In that case it is still possible to count within the counting layer 310, and by extrapolating the count signal 241 into an integration signal 251 (e.g. by multiplying the number of counts by an estimated mean energy to obtain an estimate of what the integrating signal would look like) to also obtain sufficient measurement results for reconstructing an energy-integrating slice image. Alternatively, the integration signal 251 may be interpolated for such pixels (in which the integration signal 251 is too weak) from neighbor pixels with a sufficiently high integration signal.

In another embodiment of the sensor unit the layer 310 is a direct-conversion sensing arrangement for directly converting incident x-ray radiation into electrical charge signals forming charge pulses and the layer 320 is an indirect sensing arrangement for first converting incident x-ray radiation into photons and then converting said photons into said integration signals.

Figure 6:
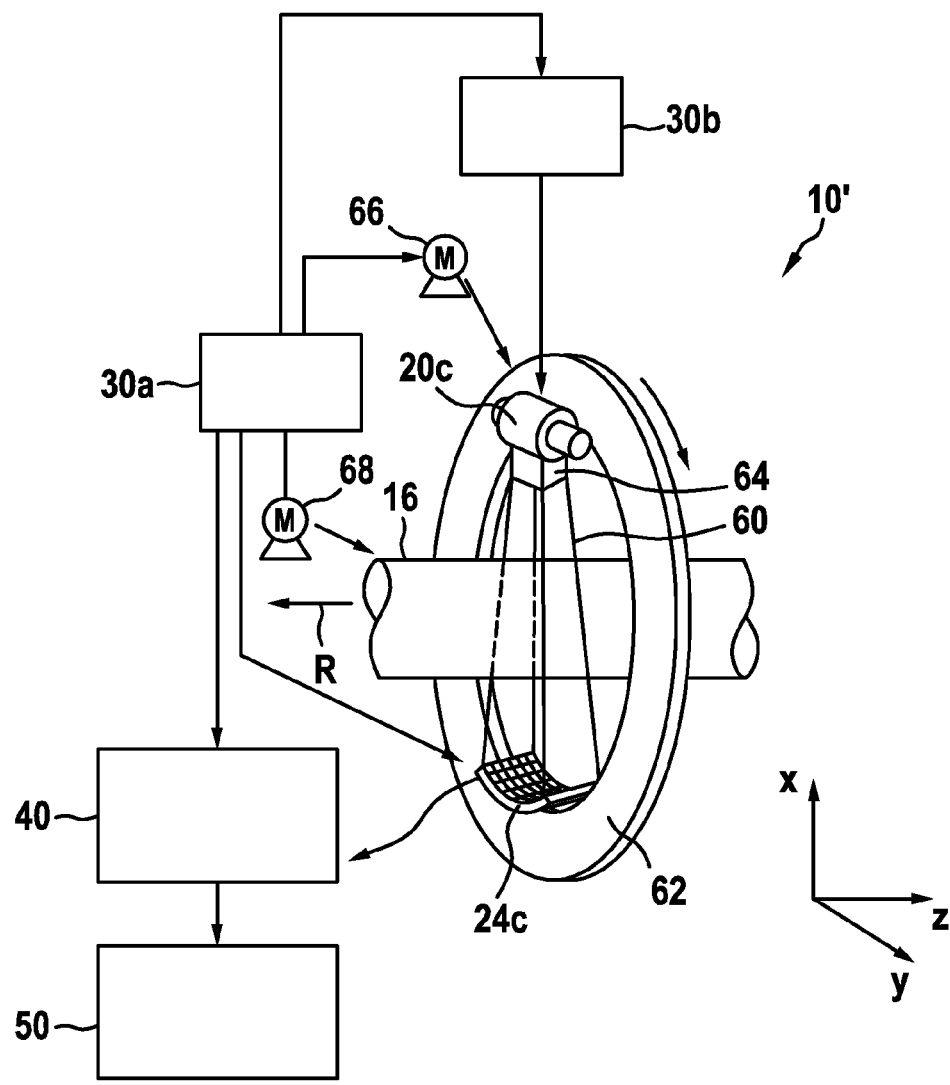
FIG. 6 shows a second embodiment of an x-ray device according to the present invention.

FIG. 6 shows a second embodiment of an x-ray device 10' according to the present invention, which is implemented as a CT imaging system for medical applications and examination of a patient. The CT imaging system shown in FIG. 1 includes a gantry 62 which is capable of rotation about an axis of rotation R which extends parallel to the z direction. The radiation source 20*c*, in particular a (conventional) polychromatic x-ray tube for emitting a broad energy spectrum of x-rays, is mounted on the gantry 62. The x-ray tube 20*c* is provided with a collimator device 64 which forms a conical radiation beam 60 from the radiation produced by the x-ray tube 20*c*. The radiation traverses an object, such as a patient 16, in a region of interest in a cylindrical examination zone (imaging region). After having traversed the examination zone, the (attenuated) x-ray beam 60 is incident on a x-ray detector unit 24*c*, in this embodiment a two-dimensional detector having a plurality of detector cells, which is mounted on the gantry 62 and which converts incident x-ray radiation into detection signals.

The gantry 62 is driven at a preferably constant but adjustable angular speed by a motor 66. A further motor 68 is provided for displacing the object, e.g. the patient 16 who is arranged on a patient table in the examination zone, parallel to the direction of the axis of rotation R or the z axis.

These motors 66, 68 are controlled by a control device 30a, for instance such that the radiation source 20c and the examination zone move relative to one another along a helical trajectory. However, it is also possible that the object or the examination zone is not moved, but that only the x-ray source 20c is rotated. Preferably, for controlling the x-ray source 20c, in particular for modulating the x-ray flux that is provided by said x-ray source 20c, a source control device 30b is provided.

The detection signals are provided to a signal processing device 40 for reconstructing an x-ray image based on the detection signals. The reconstructed image is then issued by the signal processing device 40, for instance to a display 50 for displaying the obtained image.

For overall control of the examination it is preferred that not only the motors 66, 68, but also the source control device 30b, the signal processing device 40, and the detector 24c itself are controlled by the control device 30a.

As explained above the x-ray detector 24c may be formed as a sensor unit including a x-ray conversion layer made from a scintillator element, such as GOS (Gadoliniumoxysulid) and a photo detector array (e.g., a photodiode layer) coupled to the x-ray conversion layer. However, other detector technologies may also be used for implementing the detector 24c. The imaging element (pixels) of the detector 24c usually have detector pixel sizes of about 1 mm² to 1.5 mm².

Apart from these general differences of the x-ray device 10' compared to the x-ray device 10 shown in FIG. 1 the processing device 40 and the processing of the detection signals is substantially identical to the way described above, i.e. the explanations provided in this respect for the x-ray device 10 apply analogously.

Figure 7:
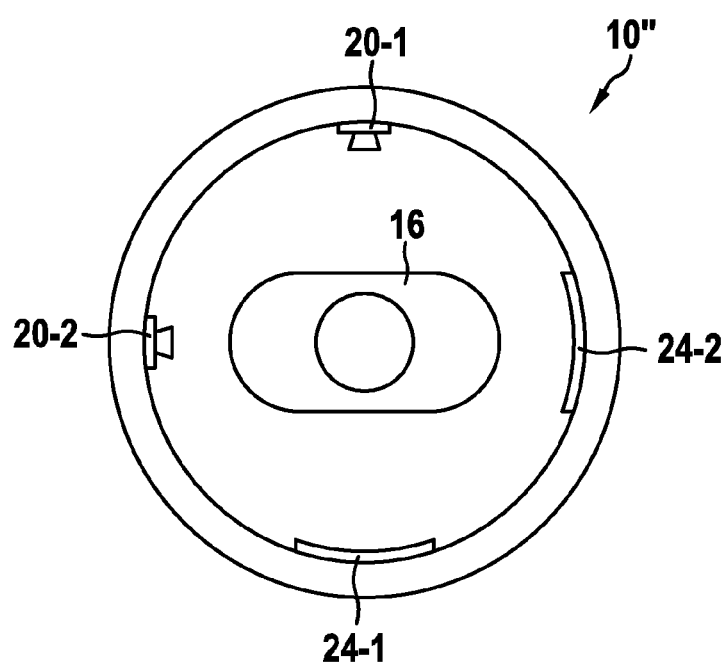
FIG. 7 shows a third embodiment of an x-ray device according to the present invention.

FIG. 7 shows still another embodiment of an x-ray device 10" according to the present invention. In this embodiment a dual source system is used comprising two x-ray sources 20-1, 20-2 and two x-ray detectors 24-1, 24-2, in which one of the detectors 24-1 is an energy-integrating detector and the other detector 24-2 is a photon-counting detector. As explained above the integration signals of the energy-integrating detector 24-1 are used to obtain the patient model especially for surface beams to estimate energy-resolved count signals of saturated pixels of the photon-counting detector 24-2.

It may, alternatively or additionally, be possible in other embodiments to use an older slice image of the patient e.g. acquired with an energy-integrating CT system for obtaining the patient model especially for surface beam.

Thus, in summary, the proposed detectors and x-ray devices provide both a counting measurement and an integrating measurement in each pixel allowing for reconstructing a slice image of the object using the integrating measurement only. This slice image can be used as a model for obtaining in "piled-up pixels", in which counting is no longer possible due to pile-up (usually the case for pixels, which see "surface beams"), an estimated (simulated) counting channel result, so that together with the counting channel measurement results of all other pixels (not piled-up) the known processing (e.g. extended Alvarez-Macovsky decomposition plus reconstruction of basis-images, bin-by-bin reconstruction of the counting channel measurement result) is possible. Thus, a dynamic beam shaper may no longer be necessary. For polarized pixels, it may be necessary to interpolate their signal from neighbor pixels, which are not polarized.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An x-ray detector comprising:
   a sensor unit for detecting incident x-ray radiation comprising a number of sensor elements,
   a counting channel per sensor element for obtaining a count signal by counting photons or charge pulses generated in response to the incident x-ray radiation since a beginning of a measurement interval,
   an integrating channel per sensor element for obtaining an integration signal representing the total energy of radiation detected since the beginning of the measurement interval, and
   a processing unit for estimating, only from the integration signals of the sensor elements and an object model, count signals of sensor elements whose counting channel has been saturated during the measurement interval.

2. The x-ray detector as claimed in claim 1, wherein said processing unit is adapted for
   determining the object model from the obtained integration signals of the sensor elements, and
   determining the estimated count signals of saturated sensor elements from said object model.

3. The x-ray detector as claimed in claim 2, wherein said processing unit is adapted for determining the estimated count signals of saturated sensor elements by
   modeling x-ray beams incident on said saturated sensor elements from the object model and a spectrum of the x-ray beams in front of the object and
   determining the estimated count signals of the saturated sensor elements from the modeled x-ray beams of the respective saturated sensor elements and non-saturated counts of x-ray beams from an air scan with a limited flux scaled according to a flux of the spectrum of the x-ray beams in front of the object.

4. The x-ray detector as claimed in claim 1, wherein said counting channel comprises at least two discriminators for counting photons or charge pulses at different energy levels since a beginning of a measurement interval and obtaining energy dependent count signals since a beginning of a measurement interval.

5. The x-ray detector as claimed in claim 1, wherein said sensor unit comprises a direct-conversion sensing layer for directly converting incident x-ray radiation into electrical charge signals forming charge pulses.

6. The x-ray detector as claimed in claim 5, wherein said sensor unit further comprises an integrating layer representing said integrating channel, said integrating layer being arranged on a side of the direct-conversion sensing layer facing away from the incident x-ray radiation for converting x-ray radiation reaching said integrating layer into said integration signals.

7. The x-ray detector as claimed in claim 6, wherein said processing unit is adapted for estimating an integration signal of a sensor element, at which insufficient x-ray radiation is reached on the integrating layer, by interpolating integration signals of neighboring sensor elements or by extrapolating the count signal of said sensor element.

8. The x-ray detector as claimed in claim 1, wherein said sensor unit comprises an indirect sensing arrangement for first converting incident x-ray radiation into photons and then converting said photons into electrical charge signals.

9. The x-ray detector as claimed in claim 1, wherein said sensor unit comprises a direct-conversion sensing arrangement for directly converting incident x-ray radiation into electrical charge signals forming charge pulses and an indirect sensing arrangement for first converting incident x-ray radiation into photons and then converting said photons into said integration signals.

10. An x-ray detection method comprising:
   detecting incident x-ray radiation by a sensor having a number of sensor elements,
   obtaining a count signal per sensor element by counting photons or charge pulses generated in response to the incident x-ray radiation since a beginning of a measurement interval and
   obtaining an integration signal per sensor element representing the total energy of radiation detected since the beginning of the measurement interval, and
   estimating, from the integration signals of the sensor elements, count signals of sensor elements whose counting channel has been saturated during the measurement interval,
   wherein said step of estimating comprises
   determining an object model from the obtained integration signals of the sensor elements, and
   determining the estimated count signals of saturated sensor elements from only said object model and the integration signals of the sensor elements.

11. An x-ray device comprising an x-ray source for emitting x-ray radiation, an x-ray detector as claimed in claim 1, and a reconstruction unit for reconstructing an image from the estimated count signals of saturated sensor elements and the obtained count signals of non-saturated sensor elements.

12. An x-ray device as claimed in claim 11, comprising at least two x-ray sources and at least two x-ray detectors, each being arranged for detecting radiation emitted by one of the at least two x-ray sources, wherein at least one detector is adapted for performing count measurements to provide count signals and at least one other detector is adapted for performing integrated measurements to provide integration signals.

13. A processor for use in an x-ray device having an x-ray detector comprising a sensor unit for detecting incident x-ray radiation comprising a number of sensor elements, a counting channel per sensor element for obtaining a count signal by counting photons or charge pulses generated in response to the incident x-ray radiation since a beginning of a measurement interval, an integrating channel per sensor element for obtaining an integration signal representing the total energy of radiation detected since the beginning of the measurement interval, said processor comprising:
   a processing unit for estimating, from the integration signals of the sensor elements, count signals of sensor elements whose counting channel has been saturated during the measurement interval, and
   a reconstruction unit for reconstructing an image from the estimated count signals of saturated sensor elements and the obtained count signals of non-saturated sensor elements,
   wherein said processing unit is adapted for
   determining an object model from the obtained integration signals of the sensor elements, and
   determining the count signals of saturated sensor elements only from said object model and the integration signals of the sensor elements.

14. A processing method for use in an x-ray device having an x-ray detector comprising a sensor unit detecting incident x-ray radiation comprising a number of sensor elements, a counting channel per sensor element for obtaining a count signal by counting photons or charge pulses generated in response to the incident x-ray radiation since a beginning of a measurement interval, an integrating channel per sensor element for obtaining an integration signal representing the total energy of radiation detected since the beginning of the measurement interval, said processing method comprising:
   estimating, from the integration signals of the sensor elements, count signals of sensor elements whose counting channel has been saturated during the measurement interval, and
   reconstructing an image from the estimated count signals of saturated sensor elements and the obtained count signals of non-saturated sensor elements,
   wherein said step of estimating comprises
   determining an object model from the obtained integration signals of the sensor elements, and
   determining the count signals of saturated sensor elements from only said object model and the integration signals of the sensor elements.

15. A non-transitory storage media comprising program code for causing a computer or processor to carry out the steps of the method as claimed in claim 14 when said program code is executed on the computer or processor.

* * * * *